(12) United States Patent
Laitinen et al.

(10) Patent No.: US 8,814,427 B2
(45) Date of Patent: Aug. 26, 2014

(54) INSTRUMENTATION AND METHOD FOR OPTICAL MEASUREMENT OF SAMPLES

(75) Inventors: Jyrki Laitinen, Kuusisto (FI); Markku Ojala, Turku (FI)

(73) Assignee: Wallac Oy, Turku (FI)

( * ) Notice: Subject to any disclaimer, the term of this patent is extended or adjusted under 35 U.S.C. 154(b) by 495 days.

(21) Appl. No.: 13/146,290

(22) PCT Filed: Oct. 13, 2009

(86) PCT No.: PCT/FI2009/050819
§ 371 (c)(1),
(2), (4) Date: Sep. 20, 2011

(87) PCT Pub. No.: WO2010/084237
PCT Pub. Date: Jul. 29, 2010

(65) Prior Publication Data
US 2012/0027044 A1    Feb. 2, 2012

Related U.S. Application Data

(60) Provisional application No. 61/149,530, filed on Feb. 3, 2009.

(30) Foreign Application Priority Data

Jan. 26, 2009  (FI) ...................................... 20095059

(51) Int. Cl.
*G01N 25/20* (2006.01)
*G01J 5/08* (2006.01)
*G01N 21/25* (2006.01)
*G01N 21/64* (2006.01)

(52) U.S. Cl.
CPC ...... *G01N 21/253* (2013.01); *G01N 2201/1211* (2013.01); *G01N 21/6452* (2013.01)
USPC ............... 374/131; 374/120; 374/1; 374/129; 250/338.1; 250/341.1; 250/341.5; 250/341.8; 356/614; 356/43

(58) Field of Classification Search
CPC ............ G01N 35/028; G01N 21/6452; G01N 21/274; G01N 21/253; G01N 2035/1039; G01N 2201/08; G01N 35/0099; G01N 35/1002; G01N 2035/0465; G01N 21/6428; G01N 21/0332; G01N 2021/0325; G01N 2021/4742; G01N 21/13; G01N 21/278
USPC ............ 374/120, 121, 124, 129, 130–132, 1, 374/10–12, 30; 250/240, 341.1, 341.5, 250/341.6, 342, 338.1, 341.8; 356/43, 614, 356/445, 434, 246
See application file for complete search history.

(56) References Cited

U.S. PATENT DOCUMENTS 4,868,148 A * 9/1989 Henk et al. ..................... 502/303
4,936,682 A * 6/1990 Hoyt ............................... 356/414
(Continued)

FOREIGN PATENT DOCUMENTS

WO    2004045772 A2    6/2004
WO    2006044972 A1    4/2006
(Continued)

OTHER PUBLICATIONS

Finnish Search Report, dated Jul. 14, 2009, from corresponding Finnish application.
(Continued)

*Primary Examiner* — Gail Verbitsky
(74) *Attorney, Agent, or Firm* — Young & Thompson

(57) ABSTRACT

An optical measurement instrument includes one or more temperature sensors (122) arranged to measure sample well specific temperatures from sample wells (111-117) arranged to store samples (103-109) to be optically measured. A processing device (121) of the optical measurement instrument is arranged to correct, using a pre-determined mathematical rule, measurement results obtained by the optical measurements on the basis of the measured sample well specific temperatures. Hence, the adverse effect caused by temperature differences between different samples on the accuracy of the temperature correction of the measurement results is mitigated.

10 Claims, 5 Drawing Sheets

(56) References Cited

U.S. PATENT DOCUMENTS

| | | | |
|---|---|---|---|
| 5,112,134 A * | 5/1992 | Chow et al. | 356/427 |
| 6,965,105 B2 * | 11/2005 | Oldham et al. | 250/236 |
| 6,977,722 B2 | 12/2005 | Wohlstadter et al. | |
| 6,982,431 B2 * | 1/2006 | Modlin et al. | 250/573 |
| 7,733,488 B1 * | 6/2010 | Johnson | 356/414 |
| 2003/0160957 A1 * | 8/2003 | Oldham et al. | 356/317 |
| 2005/0142033 A1 | 6/2005 | Glezer et al. | |
| 2005/0264805 A1 * | 12/2005 | Cromwell et al. | 356/246 |
| 2008/0117421 A1 * | 5/2008 | Yamaguchi et al. | 356/417 |
| 2010/0238431 A1 * | 9/2010 | Johnson | 356/216 |
| 2011/0043828 A1 * | 2/2011 | Frutos et al. | 356/614 |
| 2011/0211067 A1 * | 9/2011 | McKay et al. | 348/135 |
| 2012/0001089 A1 * | 1/2012 | Laitinen | 250/458.1 |
| 2012/0021424 A1 * | 1/2012 | Sandell | 435/6.12 |
| 2012/0190590 A1 * | 7/2012 | Wohlstadter et al. | 506/39 |

FOREIGN PATENT DOCUMENTS

| | | |
|---|---|---|
| WO | 2007005077 A1 | 1/2007 |
| WO | 2007138302 A1 | 12/2007 |

OTHER PUBLICATIONS

International Search Report, dated Feb. 5, 2010, from corresponding PCT application.

* cited by examiner

INSTRUMENTATION AND METHOD FOR OPTICAL MEASUREMENT OF SAMPLES

FIELD OF THE INVENTION

The invention relates to a method for improving accuracy of measurement results taken with an optical measurement instrument. An optical measurement can be, for example but not necessarily, an absorption measurement, a photoluminescence measurement, or a chemiluminescence measurement. Furthermore, the invention relates to an optical measurement instrument and to a computer program for improving accuracy of optical measurements taken with an optical measurement instrument.

BACKGROUND

The work in analytical biochemical laboratories and in clinical laboratories is often based on different tags or labels coupled on macromolecules under inspection. Typical labels used are different radioactive isotopes, enzymes, different fluorescent molecules and e.g. fluorescent chelates of rare earth metals. Detection of enzyme labels can be performed by utilizing its natural biochemical function, i.e. to alter the physical properties of molecules. In enzyme immunoassays colourless substances are catalysed by enzyme to colourful substances or non-fluorescent substances to fluorescent substances.

The colourful substances can be measured with absorption measurement, i.e. photometric measurement. In the absorption measurement the intensity of filtered and stabilized beam is first measured without any sample and then the sample inside one plate is measured. The absorbance i.e. the absorption values are then calculated.

The fluorescent substances can be measured with fluorescent measurement that is generally used for measuring quantities of fluorescent label substance in a sample. The most photoluminescence labels are based on molecular photoluminescence process. In this process optical radiation is absorbed by the ground state of a molecule. Due to the absorption of energy the quantum molecule rises into higher excited state. After the fast vibrational relaxation the molecule returns back to its ground state and the excess energy is released as an optical quantum. Due to losses in this process the average absorbed energies are higher than the average emitted energies.

A further measurement method is chemiluminescence measurement where emission of a substance is measured from a sample without excitation by illumination. Thus a photoluminometer suitable for photoluminescence measurements can also be used as a chemiluminometer.

Further, there is an analysing method called Amplified Luminescent Proximity Homogeneous Assay or AlphaScreen™. The function of the AlphaScreen™ method is based on the use of small beads that attach to the molecules under study. There are two types of beads that are coated with a material acting either as a donor or acceptor of singlet-state oxygen. The measurement starts, when the liquid sample is illuminated by light with a suitable wavelength e.g. 680 nm. After this, the material in the donor bead converts ambient oxygen into singlet-state oxygen. The single-state molecules have a short lifetime and they can reach only about a 200 nm distance by diffusion in the liquid. If the chemical reaction in question has taken place, both the donor and acceptor beads are bound to the same molecule and so they are sufficiently close to each other. In this case the singlet-state oxygen may reach the acceptor bead where a series of reactions is started. As the last phase of the reaction the coating material in the acceptor beads emits photons in the 500-700 nm range. If the chemical reaction has not taken place the singlet-state oxygen cannot reach the acceptor bead and the emission light is not detected. By measuring the intensity of light it is possible to conclude the efficiency of the chemical reaction.

An optical measurement instrument suitable for performing some or all of the measurements of the kind described above comprises typically at least one excitation light source for producing excitation beams to one or more samples to be measured at each time. Each excitation light source can be for example a flash lamp or a laser source. An optical path from an excitation light source to a sample may contain for example lenses, fibers, mirrors, dichroic mirrors, optical filters, monochromators and/or other optical elements. The optical measurement instrument further comprises at least one detector for detecting emission beams emitted by the samples to be measured at each time, and for producing detection signals responsive to the detected emission beams. The optical measurement instrument further comprises a processing device for producing a measurement result for each sample to be measured on the basis of the detection signal related to that sample. Each detector can be for example a photo-diode or a photo-multiplier tube. An optical path from the sample to the detector may contain for example lenses, fibers, mirrors, dichroic mirrors, optical filters, monochromators, and/or other optical elements. Each sample to be measured is contained by one of a plurality of sample wells that are built on e.g. a microtitration plate or another sample support element. In practical measurement circumstances temperatures of different samples may deviate from each other. The temperature deviation of different samples is a harmful phenomenon because the intensity of the emission radiation emitted by a sample depends on the temperature of the sample, and thus measurement results obtained from different samples are not commensurate with each other.

Publication U.S. Pat. No. 6,977,722 discloses an optical measurement instrument that includes one or more temperature sensors adapted to measure temperatures of a sample plate. Each temperature sensor may be a contact sensor, e.g. a temperature dependent resistor or a thermocouple, or a non-contact sensor such as an IR-sensor (infrared). The one or more temperature sensors is/are adapted to be able to measure the temperature of various locations on the sample plate, e.g. through the use of multiple sensors and/or by moving the sample plate relative to the sensors. The optical measurement instrument further comprises a computer adapted to receive the signal from the one or more temperature sensors, report the temperature to the user, and correct the measured signals to account for the effects of temperature. The accuracy of the temperature correction depends on temperature gradients on the sample plate and also on the selection of the locations on the sample plate from which the temperatures are measured.

SUMMARY

In accordance with a first aspect of the invention, there is provided a new optical measurement instrument. An optical measurement instrument according to the invention comprises:
- at least one excitation light source each of which being arranged to produce an excitation beam for at least one of samples to be measured, each sample to be measured being stored in one of a plurality of sample wells,
- at least one detector each of which being arranged to detect an emission beam emitted by one of the samples to be measured and to produce a detection signal responsive to the detected emission beam, at least one temperature sensor arranged to measure sample well specific temperatures from the sample wells, the at least one temperature sensor being capable of measuring different temperatures from different sample wells, and a processing device arranged to produce a measurement result for each sample to be measured on the basis of the detection signal related to that sample and to correct the measurement result related to each sample to be measured on the basis of the sample well specific temperature measured from the particular sample well containing that sample, wherein the plurality of the sample wells are movable with respect to the at least one temperature sensor so as to enable each temperature sensor to measure the sample well specific temperatures from more than one sample well and the at least one temperature sensor is arranged to measure the sample well specific temperature from that particular sample well that is in such a mechanical position that the detector is able to detect the emission beam emitted by the sample stored in that particular sample well.

As the measurement result related to a certain sample is corrected on the basis of the sample well specific temperature measured from the particular sample well containing the sample under inspection and each sample well specific temperature is measured when the sample under inspection is in a mechanical position enabling the detector to detect the emission beam emitted by the sample, the accuracy of the temperature correction is better than when using the optical measurement instrument according to the prior art described earlier in this document.

In accordance with a second aspect of the invention, there is provided a new method for making temperature corrections to measurement results taken with an optical measurement instrument that comprises:

at least one excitation light source each of which being arranged to produce an excitation beam for at least one of samples to be measured, each sample to be measured being stored in one of a plurality of sample wells, at least one detector each of which being arranged to detect an emission beam emitted by one of the samples to be measured and to produce a detection signal responsive to the detected emission beam, and a processing device for producing the measurement result for each sample to be measured on the basis of the detection signal related to that sample.

A method according to the invention comprises:

measuring, with a temperature sensor, sample well specific temperatures from the sample wells, correcting the measurement result related to each sample to be measured on the basis of the sample well specific temperature measured from the particular sample well containing that sample, moving the plurality of the sample wells with respect to the temperature sensor so as to enable the temperature sensor to measure the sample well specific temperatures from more than one sample well, and measuring the sample well specific temperature from each particular sample well when that particular sample well is in such a mechanical position that the detector is able to detect the emission beam emitted by the sample stored in that particular sample well.

In accordance with a third aspect of the invention, there is provided a new computer program for improving accuracy of optical measurements taken with an optical measurement instrument that comprises:

at least one excitation light source each of which being arranged to produce an excitation beam for at least one of samples to be measured, each sample to be measured being stored in one of a plurality of sample wells, at least one detector each of which being arranged to detect an emission beam emitted by one of the samples to be measured and to produce a detection signal responsive to the detected emission beam, a programmable processing device for producing a measurement result for each sample to be measured on the basis of the detection signal related to that sample, and at least one temperature sensor arranged to measure sample well specific temperatures from the sample wells, the at least one temperature sensor being capable of measuring different temperatures from different sample wells.

A computer program product according to the invention comprises processor executable instructions for controlling the programmable processing device to:

correct the measurement result related to each sample to be measured on the basis of the sample well specific temperature measured from the particular sample well containing that sample, control the plurality of the sample wells to be moved with respect to the at least one temperature sensor so as to enable each temperature sensor to measure the sample well specific temperatures from more than one sample well, and control the at least one temperature sensor to measure the sample well specific temperature from each particular sample well when that particular sample well is in such a mechanical position that the detector is able to detect the emission beam emitted by the sample stored in that particular sample well.

In accordance with a fourth aspect of the invention, there is provided a new computer readable medium that is encoded with a computer program according to the invention. The computer readable medium can be, for example, an optical disc or an electronic memory device.

A number of exemplifying embodiments of the invention are described in accompanied dependent claims.

Various exemplifying embodiments of the invention both as to constructions and to methods of operation, together with additional objects and advantages thereof, will be best understood from the following description of specific exemplifying embodiments when read in connection with the accompanying drawings.

The verb "to comprise" is used in this document as an open limitation that does not exclude the existence of also unrecited features. The features recited in depending claims are mutually freely combinable unless otherwise explicitly stated.

BRIEF DESCRIPTION OF THE FIGURES

The exemplifying embodiments of the invention and their advantages are explained in greater detail below in the sense of examples and with reference to the accompanying drawings, in which.

DESCRIPTION OF THE EMBODIMENTS

Figure 1A:
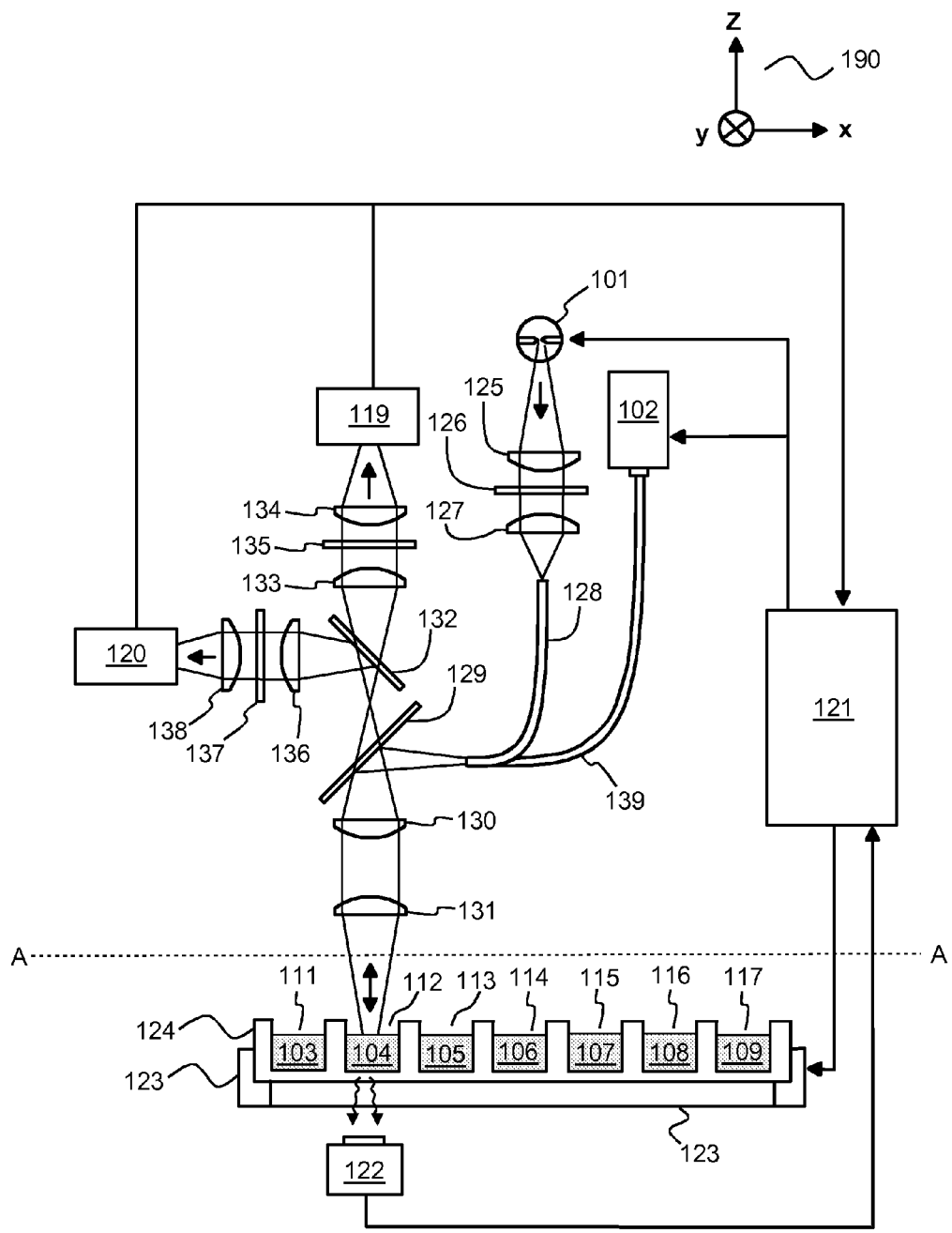
FIG. 1a shows a schematic illustration of a side view of an optical measurement instrument according to an embodiment of the invention.
Figure 1B:
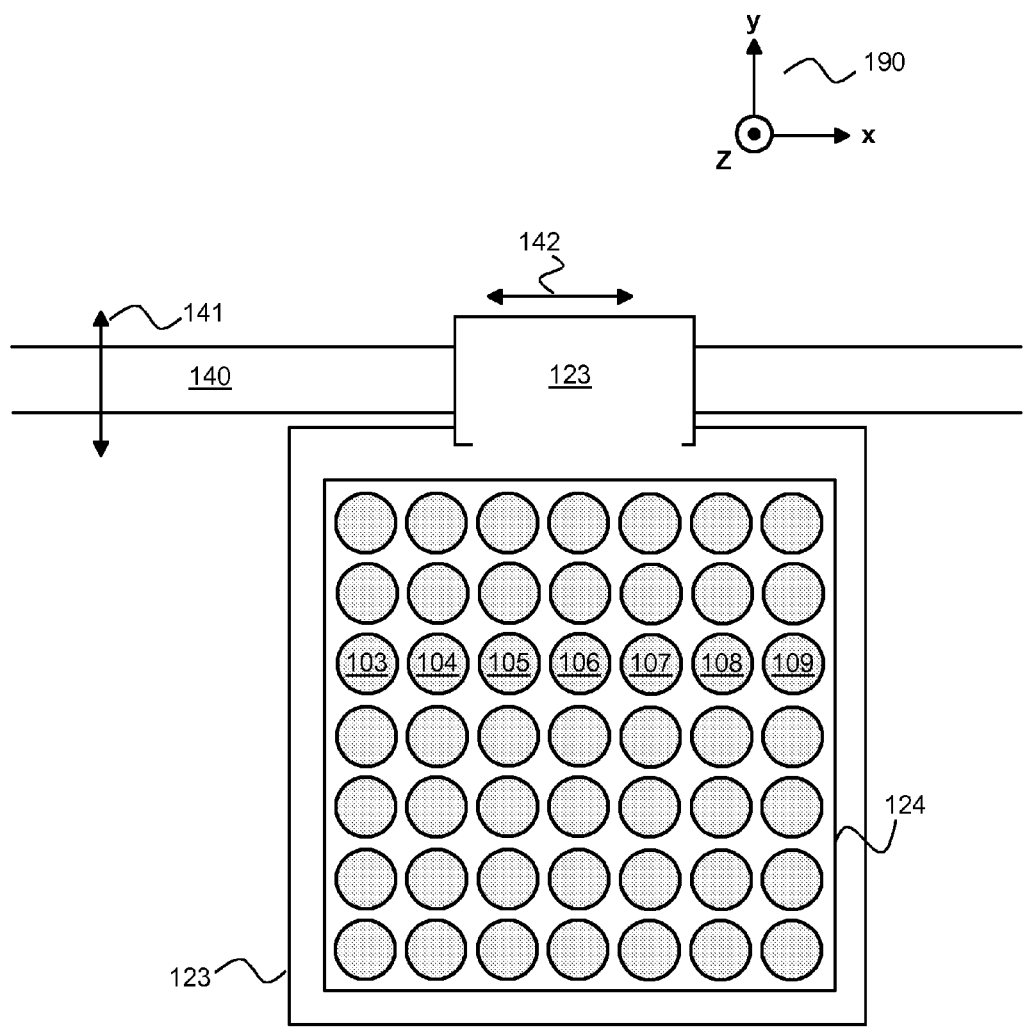
FIG. 1b shows a schematic illustration of a view seen downwards from line A-A of FIG. 1a, FIG. 2 shows a schematic illustration of a side view of an optical measurement instrument that is an alternative for the optical measurement instrument illustrated in FIGS. 1a and 1b.

FIG. 1a shows a schematic illustration of a side view of an optical measurement instrument according to an embodiment of the invention. Samples 103, 104, 105, 106, 107, 108, 109 to be measured are stored in sample wells 111, 112, 113, 114, 115, 116, 117, respectively. FIG. 1b shows a schematic illustration of a view seen downwards from line A-A of FIG. 1a. As can be seen from FIG. 1b, the sample wells constitute in this exemplifying case a 7×7 array. In many cases there are, however, more sample wells in the array, e.g. 96 sample wells. The optical measurement instrument comprises an interface device 123 for receiving a separate element 124 that includes the plurality of the sample wells. Hence, the element 124 including the sample wells is changeable. The interface device 123 is often called a sample plate sledge. The interface device 123 is mechanically connected to a support rail 140 that is movable in the directions defined by a two-headed arrow 141. The interface device 123 is in turn movable with respect to the support rail 140 in the directions defined by a two-headed arrow 142. Hence, the interface device 123 and also the sample wells are movable in the xy-plane defined by a co-ordinate system 190. Thus, each sample can be measured by changing the mechanical position of the interface device 123. In the exemplifying situation shown in FIG. 1a, a sample that is currently being measured is the sample 104 that is stored in the sample well 112. In principle it would be possible that the element 124 including the sample wells is an integral part of the optical measurement instrument but several advantages are provided by having a changeable element that includes the plurality of sample wells.

Referring to FIG. 1a, the optical measurement instrument comprises an excitation light source 101 that is arranged to produce an excitation light beam. The excitation light source 101 can be, for example, a flash lamp. The excitation light beam radiated by the excitation light source 101 is collimated with a lens 125 and directed through an optical filter 126. Different optical filters can be selected for different wavelengths. The excitation light beam is then focused with a lens 127 to an end of a fibre optic guide 128, which guides the excitation light beam to a dichroic mirror 129. The fibre optic guide can be, for example, a bundle of fibres, such as 200 pieces of fibres with a diameter of e.g. 100 μm. The bundle of fibres can be used for mixing the excitation light beam in order to avoid an uneven distribution of light on a sample to be measured. The excitation light beam is reflected by the dichroic mirror 129 to a collimating lens 130. The excitation light beam is then focused with a lens 131 to the sample 104.

Photoluminescence emission beam from the sample 104 is directed with the lenses 131 and 130 to the dichroic mirror 129. The dichroic mirror is preferably designed so that it reflects excitation wavelength but transmits emission wavelengths. The emission beam is then divided into to two beams by a second mirror 132. The mirror 132 is preferably a dichroic mirror, which functions as a filter so that an emission beam with a first emission wavelength is transmitted through the mirror and an emission beam with a second emission wavelength is reflected by the mirror. The emission beam that is transmitted through the mirror 132 is collimated with a lens 133, filtered with an optical filter 135, and focused with a lens 134 into an aperture of a detector 119. The emission beam that is reflected by the mirror 132 is collimated with a lens 136, filtered with an optical filter 137, and focused with a lens 138 into an aperture of a detector 120. The detector 119 can be for example a photo-multiplier tube and the detector 120 can be for example a photo-diode. The detectors 119 and 120 are arranged to produce first and second detection signals responsive to the detected beam with the first emission wave-length and to the detected beam with the second emission wavelength. The first and second detection signals are then amplified and processed to achieve a value for the intensities of the emission beams with the first and second emission wavelengths.

In the AlphaScreen™ measurement mode, the excitation light beam is received from an excitation light source 102 that is a laser source. The excitation light beam is guided via an optical guide 139 to the dichroic mirror 129. In the AlphaScreen™ measurement only one detector 119 is used, preferably a photomultiplier tube. In the AlphaScreen™ measurement a transparent thermo plate (not shown) is preferably used for sealing the openings of the sample wells 111-117.

The optical measurement instrument comprises a processing device 121 for producing a measurement result for each sample 103-109 to be measured on the basis of the detection signal related to that sample. The optical measurement instrument comprises temperature sensor 122 arranged to measure sample well specific temperatures from the sample wells 111-117. The element 124 including the sample wells 111-117 is movable in the xy-plane with respect to the temperature sensor 122. Thus, the temperature sensor can be used for measuring the sample well specific temperatures from all the sample wells. The temperature sensor 122 can be, for example, an IR-sensor (infrared).

In the optical measurement instrument shown in FIG. 1a, the temperature sensor 122 is arranged to measure the sample well specific temperature from that sample well 112 that is at each time in the mechanical position enabling the detector 119 and/or 120 to detect the emission beam emitted by the sample 104 stored in that sample well, i.e. the temperature sensor 122 is arranged to measure the sample well specific temperature from that sample well the sample contained by which is currently being measured. The processing device 121 is arranged to use a predetermined mathematical rule for correcting the measurement result related to each sample to be measured on the basis of the sample well specific temperature measured from the particular sample well containing that sample. The measurement result related to the sample 103 is corrected using the temperature measured from the sample well 111, the measurement result related to the sample 104 is corrected using the temperature measured from the sample well 112, etc. The measurement result M related to a certain sample can be corrected, for example, according to the following rule:

$$M_{corr} = M \times F(T), \quad (1)$$

wherein $M_{corr}$ the corrected measurement result and F(T) is a pre-determined is function of the sample well specific temperature T. The pre-determined function F(T) can be, for example $$F(T) = \alpha^{(T_0 - T)}, \quad (2)$$

wherein α is a temperature coefficient and $T_0$ is a reference temperature. If, for example, 1° C. increase in the temperature means p % increase in the measurement result M, the temperature coefficient α can be selected to be 1+p/100. With this value of α, the function F(T) is able to compensate the change in the measurement result.

In order to eliminate the effect of temporal temperature changes from the measurement results, the temperature sensor 122 is preferably is arranged to measure the sample well specific temperature during a time interval when the detector 119 and/or 120 is/are detecting the emission beam from the sample stored in the corresponding sample well, i.e. the detection of emission beam and the temperature measurement are substantially simultaneous.

Figure 2:
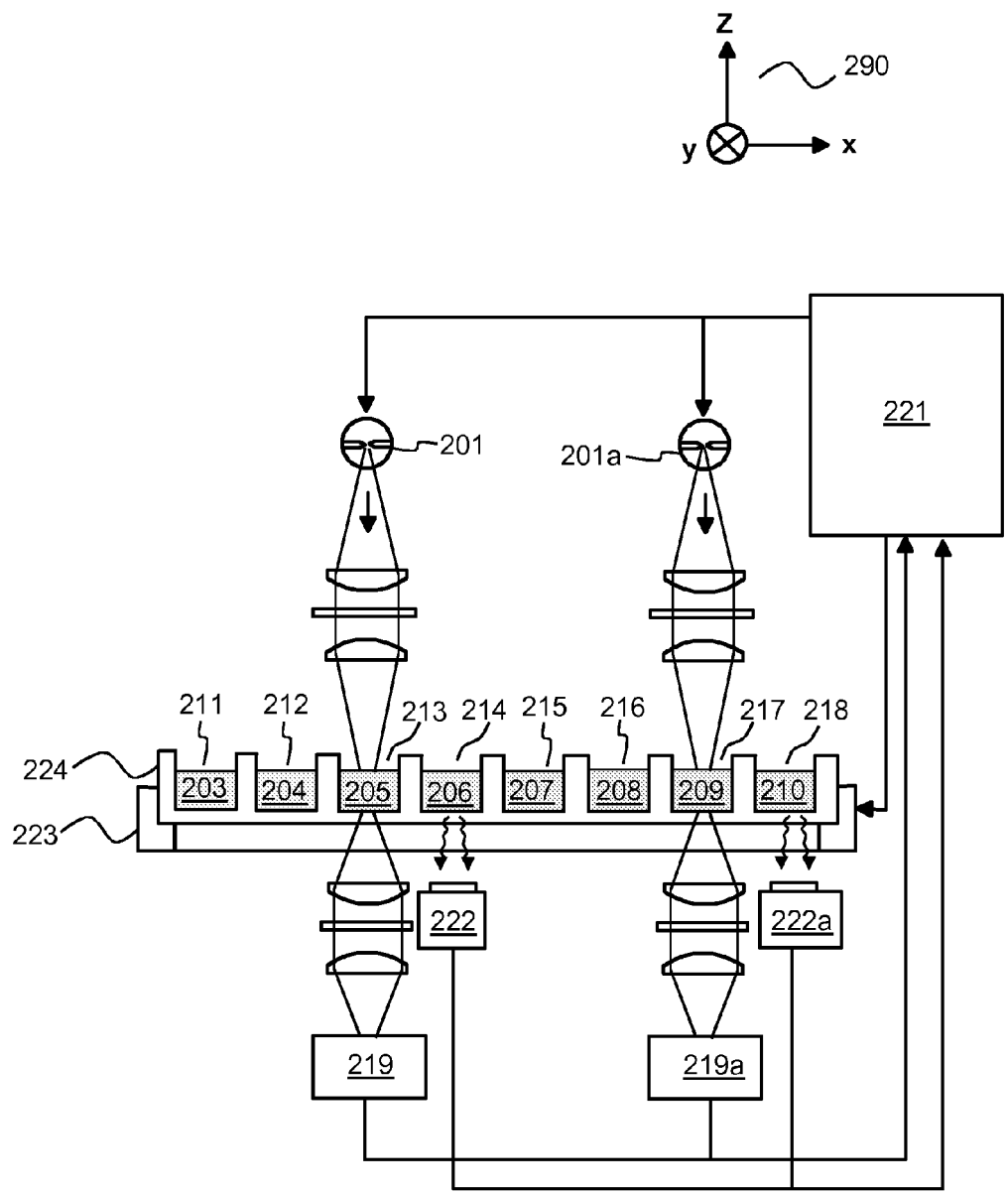

FIG. 2 shows a schematic illustration of a side view of an optical measurement instrument that is an alternative for the optical measurement instrument illustrated in FIGS. 1a and 1b. Samples 203, 204, 205, 206, 207, 208, 209, 210 to be measured are stored in sample wells 211, 212, 213, 214, 215, 216, 217, 218, respectively. The optical measurement instrument comprises an interface device 223 for receiving a separate element 224 that includes the sample wells. The interface device 223 and thus also the sample wells are movable in the xy-plane defined by a co-ordinate system 290.

The optical measurement instrument comprises measurement arrangements that allow simultaneous measurement of two samples. In the exemplifying situation shown in FIG. 2, the samples 205 and 209 are currently being measured. The sample 205 is illuminated with an excitation light source 201 and the sample 209 is illuminated with an excitation light source 201a. It is also possible to use a single excitation light source for illuminating more than one sample simultaneously. For example, fibre optic guides can be used for dividing the light radiated by a single excitation light source for several samples. An emission beam emitted by the sample 205 is detected with a detector 219 and an emission beam emitted by the sample 209 is detected with a detector 219a. The detectors 219 and 219a are arranged to produce detection signals responsive to the detected emission beams.

The optical measurement instrument comprises a processing device 221 for producing a measurement result for each sample to be measured on the basis of the detection signal related to that sample. The optical measurement instrument further comprises temperature sensors 222 and 222a arranged to measure sample well specific temperatures from the sample wells. The processing device 221 is arranged to correct the measurement result related to each sample on the basis of the sample well specific temperature measured from the particular sample well containing that sample.

In the optical measurement instrument shown in FIG. 2, the temperature sensor 222 is arranged to measure the sample well specific temperature from the sample well 214 that is adjacent to the sample well 213 containing the sample 205 currently being measured. Correspondingly, the temperature sensor 222a is arranged to measure the sample well specific temperature from the sample well 218 that is adjacent to the sample well 217 containing the sample 209 currently being measured. For the sake of illustration, we can consider a situation in which the sample wells 211 and 215 are directly above the temperature sensors 222 and 222a, respectively. This situation is not the one depicted in FIG. 2. In the above-mentioned situation, the temperatures can be measured from the sample wells 211 and 215. After this, the sample wells are shifted one step leftwards and the temperatures are measured from the sample wells 212 and 216 simultaneously with detecting emission beams from the samples 203 and 207, then the sample wells are shifted again one step leftwards and the temperatures are measured from the sample wells 213 and 217 simultaneously with detecting emission beams from the samples 204 and 208, then the sample wells are shifted again one step leftwards and the situation becomes the one depicted in FIG. 2, and so on. The measurement result related to the sample 203 is corrected using the temperature measured from the sample well 211, the measurement result related to the sample 204 is corrected using the temperature measured from the sample well 212, etc. Hence, the measured temperatures represent somewhat old information from the viewpoint of correcting the measurement results, but in many practical cases the resulting error is sufficiently small, because temporal temperature changes are typically slow relative to time between temporally successive measurements.

Figure 3:
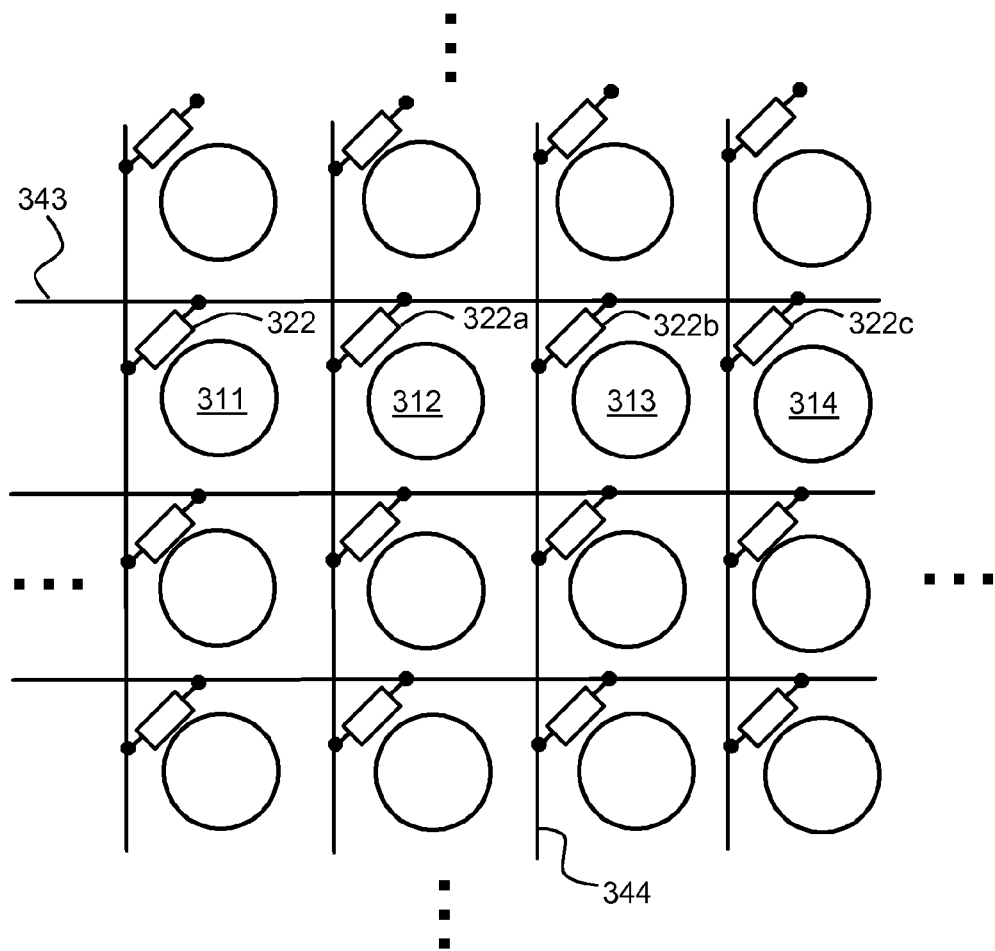
FIG. 3 shows a schematic illustration of a temperature sensor arrangement that is suitable for an optical measurement instrument that is an alternative for the optical measurement instrument illustrated in FIGS. 1a and 1b.

FIG. 3 shows a schematic illustration of a temperature sensor arrangement that is suitable for an optical measurement instrument that is an alternative for the optical measurement instrument illustrated in FIGS. 1a and 1b. The temperature sensor arrangement comprises a separate temperature sensor 322, 322a, 322b, 322c for each of the sample wells 311, 312, 313, 314. The temperature sensors can be integrated with an element including the sample wells or with an interface device for receiving a separate element that includes the sample wells. The temperature sensors can be, for example, temperature sensitive resistors such as NTC-resistors or PTC-resistors (negative temperature coefficient, positive temperature coefficient) or thermocouples. In the temperature sensor arrangement shown in FIG. 3, the temperature dependent resistance or voltage value of the temperature sensor 322b can be detected between electrical wires 343 and 344.

Figure 4:
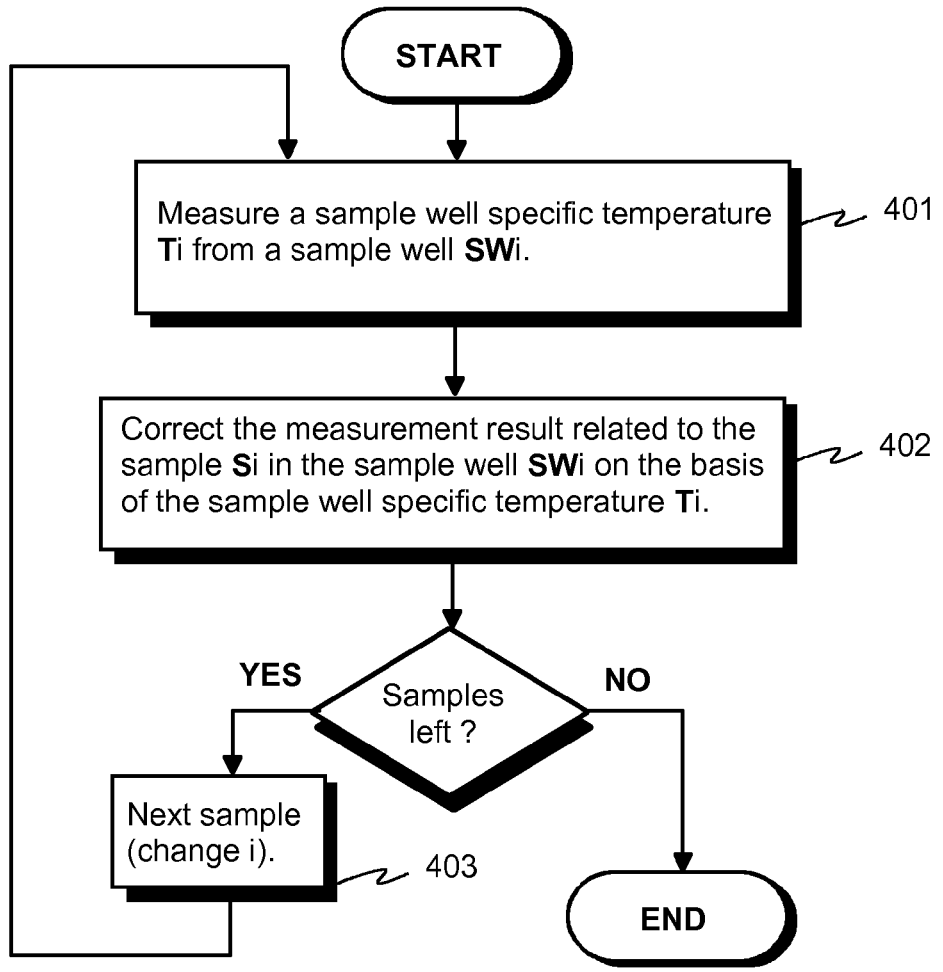
FIG. 4 is a flow chart of a method according to an embodiment of the invention for improving accuracy of optical measurements taken with an optical measurement instrument.

FIG. 4 is a flow chart of a method according to an embodiment of the invention for improving accuracy of optical measurements taken with an optical measurement instrument that comprises:
- at least one excitation light source each of which being arranged to produce an excitation beam for at least one of samples to be measured, each sample to be measured being stored in one of a plurality of sample wells,
- at least one detector each of which being arranged to detect an emission beam emitted by one of the samples to be measured and to produce a detection signal responsive to the detected emission beam, and
- a processing device for producing the measurement result for each sample to be measured on the basis of the detection signal related to that sample.

The method comprises in phase 401 measuring a sample well specific temperature $T_i$ from a sample well $SW_i$. The method comprises in phase 402 correcting, using a pre-determined mathematical rule, the measurement result related to the sample $S_i$ stored in the sample well $SW_i$ on the basis of the sample well specific temperature $T_i$. The method comprises in phase 403 continuing with a next sample if there are samples to be measured left.

In a method according to an embodiment of the invention, the sample well specific temperature is measured during a time interval when the detector is detecting the emission beam from the sample stored in the corresponding sample well.

In a method according to an embodiment of the invention, the at least one temperature sensor comprises a separate temperature sensor for each of the sample wells.

In a method according to an embodiment of the invention, the plurality of the sample wells are moved with respect to the temperature sensor so as to enable the temperature sensor to measure the sample well specific temperatures from more than one sample well.

In a method according to an embodiment of the invention, the sample well specific temperature is measured from each particular sample well when that sample well is in a mechanical position enabling the detector to detect the emission beam emitted by the sample stored in that sample well.

In a method according to an embodiment of the invention, the measurement result related to each sample to be measured is corrected according to the following rule:

$$M_{corr} = M \times F(T),$$

wherein $M_{corr}$ is the corrected measurement result, M is the measurement result, and F(T) is a pre-determined function of the sample well specific temperature T that is measured from the particular sample well containing the sample under consideration.

In a method according to an embodiment of the invention, the measurement result related to each sample to be measured is corrected according to the following rule:

$$M_{corr} = M \times \alpha^{(T0-T)},$$

wherein $M_{corr}$ is the corrected measurement result, M is the measurement result, $\alpha$ and $T_0$ are predetermined constants, and T is the sample well specific temperature that is measured from the particular sample well containing the sample under consideration.

A computer program according to an embodiment of the invention comprises software means for improving accuracy of optical measurements taken with an optical measurement instrument that comprises:
- at least one excitation light source each of which being arranged to produce an excitation beam for at least one of samples to be measured, each sample to be measured being stored in one of a plurality of sample wells,
- at least one detector each of which being arranged to detect an emission beam emitted by one of the samples to be measured and to produce a detection signal responsive to the detected emission beam,
- a programmable processing device for producing a measurement result for each sample to be measured on the basis of the detection signal related to that sample, and
- at least one temperature sensor arranged to measure sample well specific temperatures from the sample wells, the at least one temperature sensor being capable of measuring different temperatures from different sample wells.

The software means comprises processor executable instructions for controlling the programmable processing device to correct, with a pre-determined mathematical rule, the measurement result related to each sample to be measured on the basis of the sample well specific temperature measured from the particular sample well containing that sample.

A computer readable medium according to an embodiment of the invention is encoded with a computer program according to an embodiment of the invention. The computer readable medium can be, for example, an optical disc or an electronic memory device.

The specific examples provided in the description given above should not be construed as limiting. Therefore, the invention is not limited merely to the embodiments described above.

What is claimed is:

1. An optical measurement instrument comprising:
   at least one excitation light source (101, 102) each of which being arranged to produce an excitation beam for at least one of samples (103-109, 203-210) to be measured, each sample to be measured being stored in one of a plurality of sample wells (111-117),
   at least one detector (119, 120) each of which being arranged to detect an emission beam emitted by one of the samples to be measured and to produce a detection signal responsive to the detected emission beam,
   a processing device (121) for producing a measurement result for each sample to be measured on the basis of the detection signal related to that sample, and
   at least one temperature sensor (122) arranged to measure sample well specific temperatures from the sample wells, the at least one temperature sensor being capable of measuring different temperatures from different sample wells, and the processing device is arranged to correct the measurement result related to each sample to be measured on the basis of the sample well specific temperature measured from the particular sample well containing that sample,
   wherein the plurality of the sample wells (111-117) are movable with respect to the at least one temperature sensor (122) so as to enable each temperature sensor to measure the sample well specific temperatures from more than one sample well, and the at least one temperature sensor is arranged to measure the sample well specific temperature from a particular one of the sample wells (112) that is in such a mechanical position that the detector (119, 120) is able to detect the emission beam emitted by the sample stored in that particular sample well.

2. The optical measurement instrument according to claim 1, wherein the temperature sensor is arranged to measure the sample well specific temperature during a time interval when the detector is detecting the emission beam from the sample stored in the corresponding sample well.

3. The optical measurement instrument according to claim 1, comprising an interface device (123, 223) for receiving a separate element (124, 224) including the plurality of the sample wells.

4. The optical measurement instrument according to claim 1, comprising an element including the plurality of the sample wells.

5. The optical measurement instrument according to claim 1, wherein the processing device is arranged to correct the measurement result related to each sample to be measured according to the following rule:

$$M_{corr} = M \times F(T),$$

wherein $M_{corr}$ is the corrected measurement result, M is the measurement result, and F(T) is a pre-determined function of the sample well specific temperature T measured from the particular sample well containing the sample under consideration.

6. The optical measurement instrument according to claim 1, wherein the processing device is arranged to correct the measurement result related to each sample to be measured according to the following rule:

$$M_{corr} = M \times \alpha^{(T0-T)},$$

wherein $M_{corr}$ is the corrected measurement result, M is the measurement result, $\alpha$ and $T_0$ are predetermined constants, and T is the sample well specific temperature measured from the particular sample well containing the sample under consideration.

7. A method for making temperature corrections to measurement results taken with an optical measurement instrument that comprises:
   at least one excitation light source each of which being arranged to produce an excitation beam for at least one of samples to be measured, each sample to be measured being stored in one of a plurality of sample wells,
   at least one detector each of which being arranged to detect an emission beam emitted by one of the samples to be measured and to produce a detection signal responsive to the detected emission beam, and a processing device for producing the measurement result for each sample to be measured on the basis of the detection signal related to that sample, the method comprising:

measuring (401), with a temperature sensor, sample well specific temperatures from the sample wells, and correcting (402) the measurement result related to each sample to be measured on the basis of the sample well specific temperature measured from the particular sample well containing that sample, wherein the method further comprises:

moving the plurality of the sample wells with respect to the temperature sensor so as to enable the temperature sensor to measure the sample well specific temperatures from more than one sample well, and measuring the sample well specific temperature from each particular sample well when that particular sample well is in such a mechanical position that the detector is able to detect the emission beam emitted by the sample stored in that particular sample well.

8. The method according to claim 7, wherein the sample well specific temperature is measured during a time interval when the detector is detecting the emission beam from the sample stored in the corresponding sample well.

9. The method according to claim 7, wherein the measurement result related to each sample to be measured is corrected according to the following rule:

$$M_{corr} = M \times F(T),$$

wherein $M_{corr}$ is the corrected measurement result, M is the measurement result, and F(T) is a pre-determined function of the sample well specific temperature T measured from the particular sample well containing the sample under consideration.

10. The method according to claim 7, wherein the measurement result related to each sample to be measured is corrected according to the following rule:

$$M_{corr} = M \times \alpha^{(T0-T)},$$

wherein $M_{corr}$ is the corrected measurement result, M is the measurement result, $\alpha$ and $T_0$ are predetermined constants, and T is the sample well specific temperature measured from the particular sample well containing the sample under consideration.

* * * * *